United States Patent
Maldonado Bas

(10) Patent No.: US 6,220,247 B1
(45) Date of Patent: Apr. 24, 2001

(54) METHOD OF TREATMENT OF GLAUCOMA WITH AN EXCIMER LASER

(76) Inventor: Arturo Rodolfo Del Rosario Maldonado Bas, Achaval Rodriguez 544, Cordoba (AR), 5000

( * ) Notice: Subject to any disclaimer, the term of this patent is extended or adjusted under 35 U.S.C. 154(b) by 0 days.

(21) Appl. No.: 09/028,555

(22) Filed: Feb. 24, 1998

Related U.S. Application Data

(60) Provisional application No. 60/062,499, filed on Oct. 20, 1997, now abandoned.

(51) Int. Cl.[7] .................................................. A61B 19/00
(52) U.S. Cl. .............................................. 128/898; 606/6
(58) Field of Search ............................ 128/898; 606/4–6, 606/166, 2–3, 10–13

(56) References Cited

U.S. PATENT DOCUMENTS

| | | |
|---|---|---|
| 5,370,641 | 12/1994 | O'Donnell, Jr. . |
| 5,549,598 | 8/1996 | O'Donnell, Jr. . |

OTHER PUBLICATIONS

LaserSight Technologies, Inc., *Laserlight Protocol For Treatment of Glaucoma*, Mar. 27, 1997.

*Primary Examiner*—David J. Isabella
*Assistant Examiner*—Kelly O'Hara
(74) *Attorney, Agent, or Firm*—Darby & Darby

(57) ABSTRACT

A method of performing trabeculodissection to treat glaucoma uses a galvanometric scanning laser delivery system. A scleral flap is cut to expose the treatment area of the trabecular meshwork. The arc of the treatment area is made as wide as the trabecular meshwork limited by the circumference of the limbal area around the patient's eye. A laser, preferably of the excimer type, is used to treat small test areas in successive discrete zones along the arc of the treatment area in the bed of the scleral flap to determine the precise depth of ablation required over the entirety of each zone to promote filtration without penetration of the treatment zone. The laser then treats discrete zones over the length of the arc to remove in scan layers so as to process discrete ablated zones of minimal residual thickness. The treatment of successive zones allows ablation along the length of the treatment arc without interference from actively draining aqueous. After ablation of the various successive zones, the scleral flap is closed and, if necessary, sutured.

19 Claims, 8 Drawing Sheets

(8 of 8 Drawing Sheet(s) Filed in Color)

METHOD OF TREATMENT OF GLAUCOMA WITH AN EXCIMER LASER

This application claims benefit of provisional application 60/062,499 Oct. 20, 1997 now abandoned.

FIELD OF THE INVENTION

The invention relates to the surgical treatment of glaucoma using a laser.

BACKGROUND OF THE INVENTION

In an open angle glaucoma, the ocular hypertension is due to an increase of the resistance to the aqueous humor outflow at the trabeculum level. Pigmentary and pseudoexfoliative types glaucoma are also subject to this effect. The Laser Trabecular Dissection (LTD) has had excellent results in treating the above-mentioned types of glaucoma. The Laser Trabecular Dissection (LTD) has not yet been totally proven in congenital, neovascular or any other type of glaucoma in which a fibrovascular or mesoderm tissue is placed between the trabeculum and the anterior chamber.

In U.S. Pat. No. 5,549,598 to O'Donnell a method is disclosed for controlling open angle glaucoma by surgery. A laser is used in the surgery to reduce the thickness of the trabecular meshwork and tissue around Schleman's Canal to increase filtration of the aqueous human and thereby control the open angle glaucoma. The surgical treatment is used as an alternative to treatment with different drugs, which potentially have adverse side affects. In the patentee's description, reference is made to surgical treatment, described as the laser trabeculoplasty technique with an argon laser, and there is an analysis of its action and clinical results.

The O'Donnell patent discusses that the pressure decrease may be transient and, in such cases, he goes on to filtrating techniques within which the trabeculectomy is the selected one, and then he goes on with the description of this technique.

In U.S. Pat. No. 5,370,641 to O'Donnell, energy in the ultraviolet wavelenght under 230 nonometers is used to perform the trabeculodissection. The preferred embodiment of this patent utilizes a galvanometric scanning system (GSS) rather than a variable opening (iris diaphragm) delivery system. Examples given of the GSS are the Compak 200 Mini excimer and the Laserharmonic, both manufactured by Lasersight, Inc. (Orlando, Fla.). As described, the advantages of a galvonometric scanning delivery system are rooted in the anatomy of the portion of the eye to be treated and also in the programmable features of the system. As shown in FIG. 1 of that patent, the anatomy of the portion of the limbal area to be treated is characterized by a curvilinear shape with a radius of approximately 7.5 mm. The arc lenght and width of treatment in the corneal scleral bed partially is determined by the severity of the glaucoma; the more severe glaucoma requires a broader and longer arc of trabeculodissection. The width is limited by the fact that the average maximum width of the trabecular meshwork is less than 1 mm. The arc is limited by the circumference of the limbal area around the eye.

Moreover, the trabecular mesh work is covered by a uneven amount of corneoscleral tissue. Specifically, the anterior most portion near the scleral septum is deeper and thinner than is the posterior portion near the scleral spur (iris root). The latter portion is more superficial and thicker. In addition, the ablation rate of corneal tissue is different from scleral tissue.

The goal of laser trabecular dissection (LTD) is to achieve as wide an area (anteroposterior) as possible of partial thickness dissection over the trabecular meshwork, especially the posterior portion, sufficiently deep to allow for adequate aqueous drainage, but not so deep that the dissection enters the anterior chamber.

A galvanometric scanning delivery system (GSS) is ideally suited to meet the above objectives. Specifically, the laser is programmed for a low, but suprathreshold, power, typically less than 120 $mj/cm^2$, to reduce the risk of full thickness penetration. The pulse frequency is set, typically at 60 to 300 Hertz, to achieve as rapid a rate of ablation as possible so as to reduce the potential for slow filtration that could absorb the laser energy and mask the laser effects. The GSS also allows selection of small spot size, in the range to 100 to 300 microns.

Variable aperture delivery system cannot be programmed to archive an appropriate ablation profile. The lack of a homogenous energy profile can create hot and cold spots and increase the risk of full perforation. Moreover, the attendant acoustic shock wave promotes premature drainage of aqueous that interferes with the ablation.

Furthermore, prior art laser trabeculodissection has an endpoint. When filtration begins, the aqueous humor absorbs the laser energy and masks the laser's effect. It would be beneficial, therefore, to use a method of surgery that allows filtration to proceed at one ablation site without interfering with the laser energy at a subsequent site.

As disclosed above, O'Donnell has used a galvanometric scanning delivery system to achieve trabeculodissection, and his method provides a plurality of test zones across the width and lenght of the treatment so that the system can be programmed to provide the optimum level dissection across a treatment area of variable thickness. O'Donnell performs the ablation in zones based upon the results of a test zone to obtain ablation without perforation and his method utilizes a relatively low power to reduce the risk of inadvertent full-thickness perforation into the anterior chamber.

The method of O'Donnell avoids acoustic shock waves, and the laser system has a homogenous energy profile and removes tissue in scan layers to process zones of minimal thickness.

Thus, it is well known from the prior art to provide a method of performing trabeculodissection using a galvanometric scanning laser delivery system. The surgeon uses a knife, such as a diamond knife and scleral dissector to make a scleral flap and expose the treatment arc of trabecular meshwork. The arc of the treatment area is as wide as the trabecular meshwork and lenght of the arc is limited by the circumference of the limbal area around the patient's eye. The surgeon uses the laser to treat small test areas in successive discrete zones along the arc of the treatment area in the bed of the scleral flap to determine the precise depth of ablation required over each entire zone so as to promote filtration without penetration of the treatment zone. The laser then is programmed to treat the length of the arc in discrete zones. Tissue is removed in scan layers, typically 2 microns thick, so as to process discrete ablated zones of minimal residual thickness. The treatment of successive zones allows ablation along the lenght of the treatment arc without interference from actively draining aqueous. After ablation of the various successive zones, the scleral flap is closed and, if necessary, sutured.

Between 1946 and 1949, Goldman was the first one to make a precise experiment to determine the place of the aqueous humor outflow resistance. He found that the place was the trabeculum. Grant performed perfusion experiments in enucleated human eyes between 1955–1958. Keeping up a continuous flow in the anterior chamber, he extirpated the trabeculum in 360° at the Schlemm channel level to find out that resistance diminished in a 75%(S). Seiler, between 1985–1988, was the first to perform a partial trabeculectomy with an excimer laser. He learned that 94% of the resistance was in the last 10 microns of the yuxtacanalicular tissue (B).

In 1993, Arenas Archillas published the AB outer trabeculectomy procedure, that is, a manual trabeculodissection procedure and the direct precedent of laser trabecular dissection (LTD). Later on, he modified his own technique employing a diamond drill and adding 0.04 mg/cc Mitomycin (Highlight 216–226).

The literature leads to the conclusion that all surgical procedures tend to eliminate or reduce the aqueous outflow resistance. The most current glaucoma surgery employed at the moment is the trabeculectomy described by Cairns in 1968.

The glaucoma technique by surgery that is presently in use is the trabeculectomy. This surgical procedure consists of performing a conjunctival incision (fornix or limbar based), to free the sclera area near the sclera-corneal limbus. A lamellar scleral flap is (300 to 400 micron thick), which is rectangular, triangular or circular, with its base directed to the cornea. Hereafter, this flap is referred to as the scleral roof. Once the scleral flap is bent over the cornea, part of the deep sclera (scleral floor), which can be about 3×2 mm rectangular, is cut out to expose the trabeculum zone and the Schlemm channel (normal drainage that are in part or completely blocked). With this a fistul is established in the intrascleral space. After performing a basal iridectomy, the scleral flap is repositioned and sutured. The conjunctiva is also sutured.

With this procedure, a valved mechanism of filtration is established by means of which aqueous humor has free access throughout the anterior chamber, the intrascleral space and subjunctival space with the consequent regulation of intraocular pressure.

The disadvantages of this technique are that, since it is an intraocular procedure, the eye is abruptly decompressed in making the 2.5 to 3 mm opening. This may result in a serious surgical accident, such as vitreous loss and even an expulsive hemorrhage that may be responsible for surgical failure, or even total visual loss.

OBJECTS OF THE INVENTION

It is therefore an object of the invention to provide a procedure of extraocular glaucoma surgery wherein all the above drawbacks and risks for the patient are avoided or, at least diminished.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

Other objects and advantages of the present invention will become more apparent upon reference to the following Specification and annexed drawings in which.

DETAILED DESCRIPTION OF THE INVENTION

Figure 1:
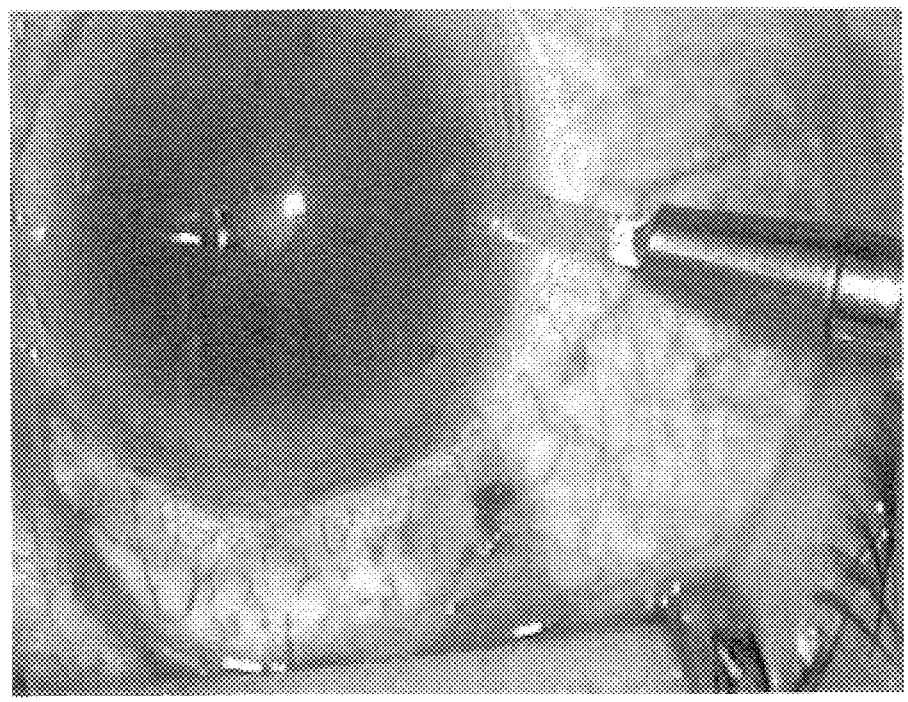
FIG. 1 is a view of conjunctival incision with a fornix base—Paracenthesis.

The present invention is based on Arenas Archilla's procedure in which the glaucoma surgery is completely, or almost completely, extraocular, thereby preventing the occurrence of the above-mentioned complications.

The procedure of the invention is described in the sequence of steps, referring to the drawings.

1. The surgery is preferably performed with topical anesthesia. This lessens the risks that a local anesthesia has and it allows a faster recovery.

2. A paracenthesis (small penetrating corneal incision) is made (FIG. 1).

3. A fornix or limbus based conjuctival incision is performed (FIG. 2) dissecting Tenon's capsule.

Figure 2:
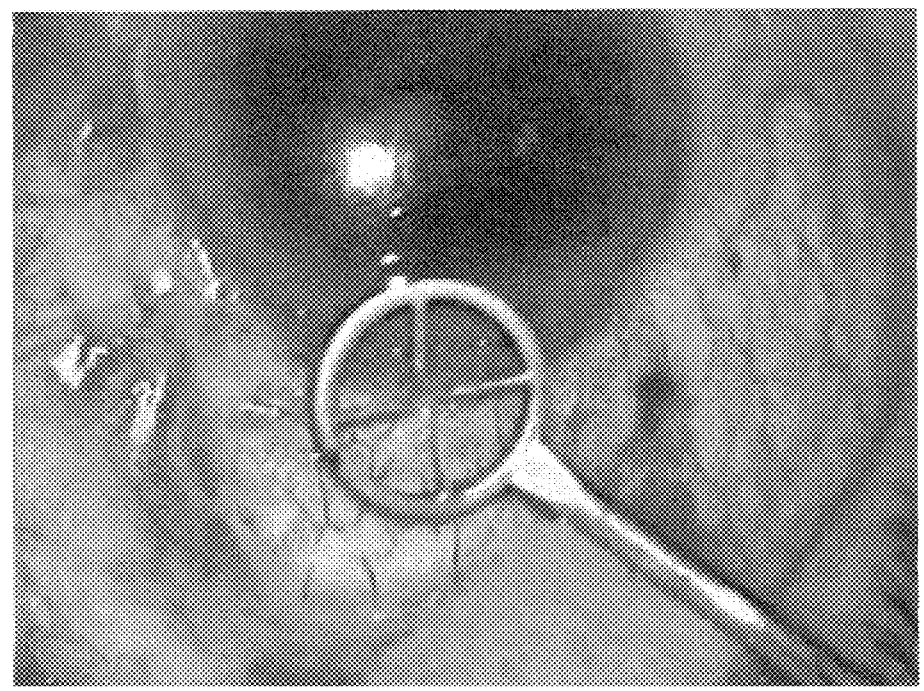
FIG. 2 shows the optic zone 4.25 mm marker for drawing flap location.
Figure 3:
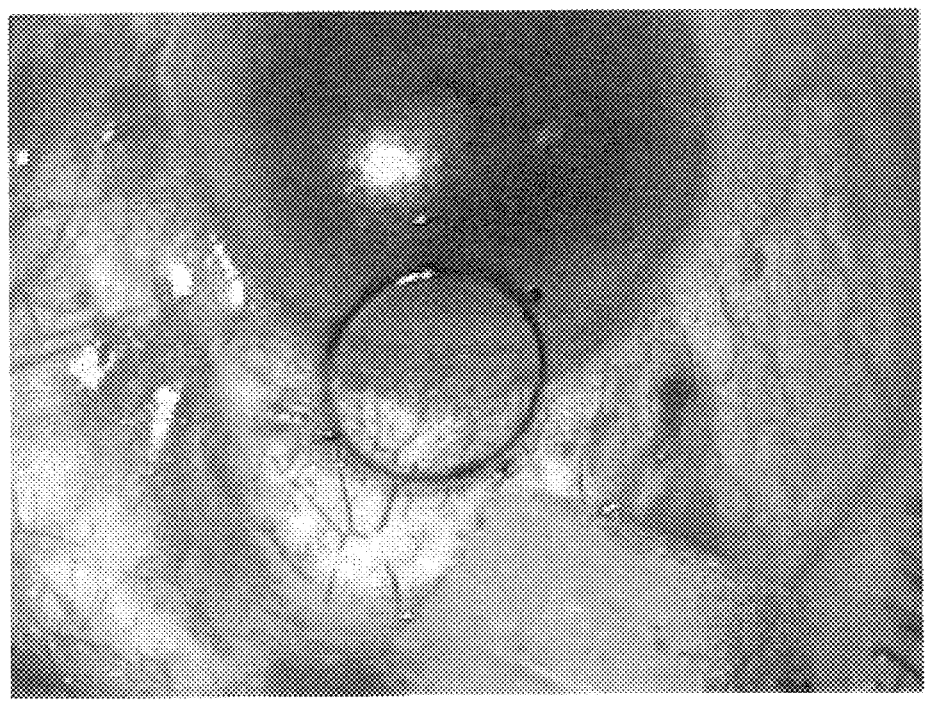
FIG. 3 shows the flap location tinted with a viewing enhancement agent.

4. Although the scleral incision of step 2. may have a rectangular, round or triangular shape, as described above, the procedure is preferably performed with a semicircular flap previously marked with the help of a 4.25 mm optic zone marker (FIGS. 2–3).

Figure 4:
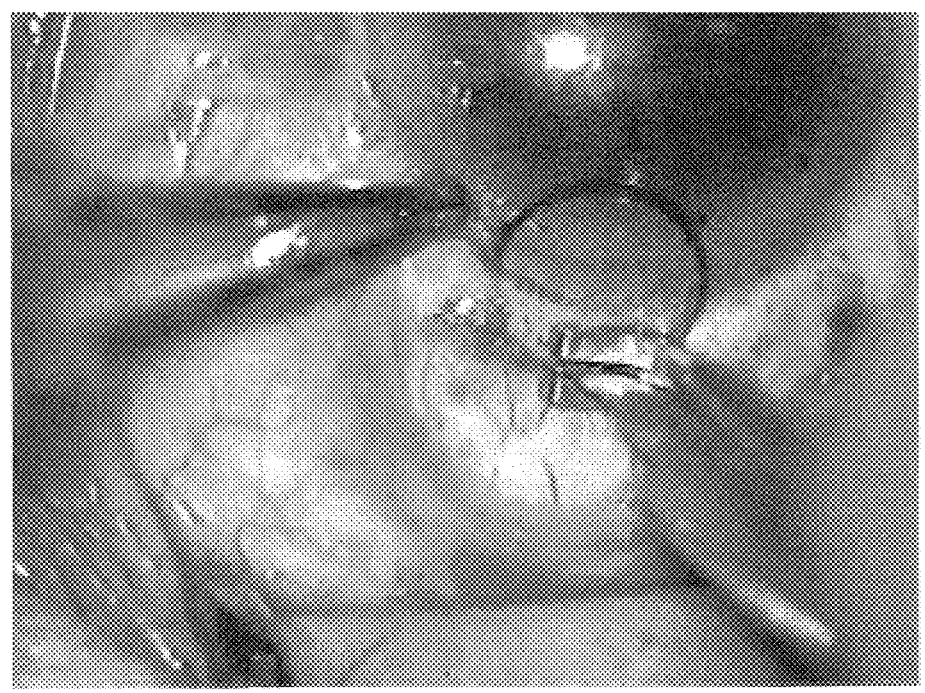
FIG. 4 shows the scleral incision.

5. With a radial keratotomy (RK) diamond knife, calibrated for 350 to 400 microns, a cut is performed beginning in the cornea and making a semicircular cut to reach the opposite side (FIG. 4). This step achieves uniformity in depth and, consequently, in the thickness of the scleral flap obtained.

Figure 5:
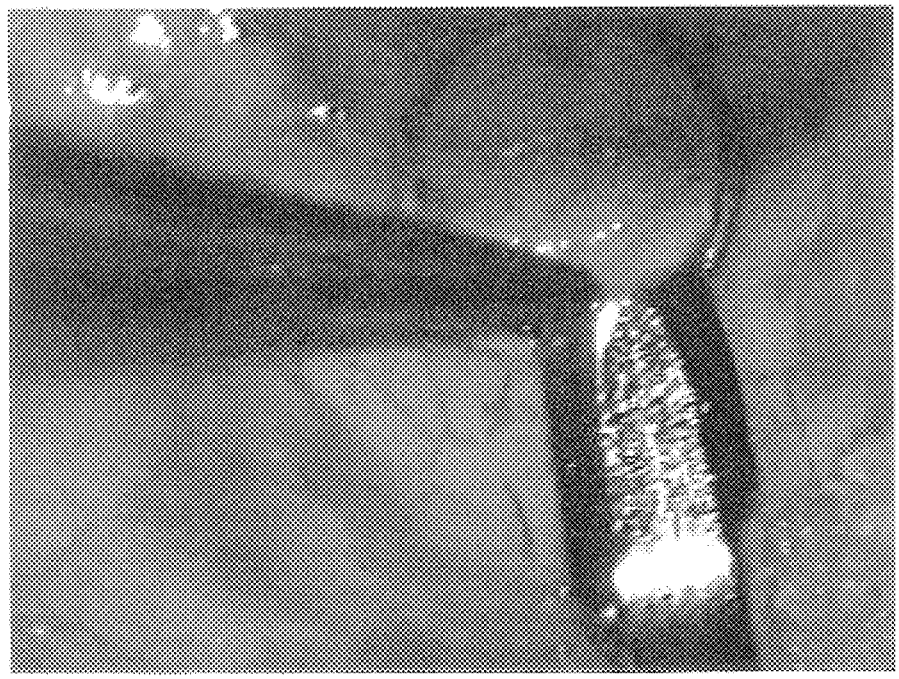
FIG. 5 shows the scleral flap upon being dissected with a crescent knife.
Figure 6:
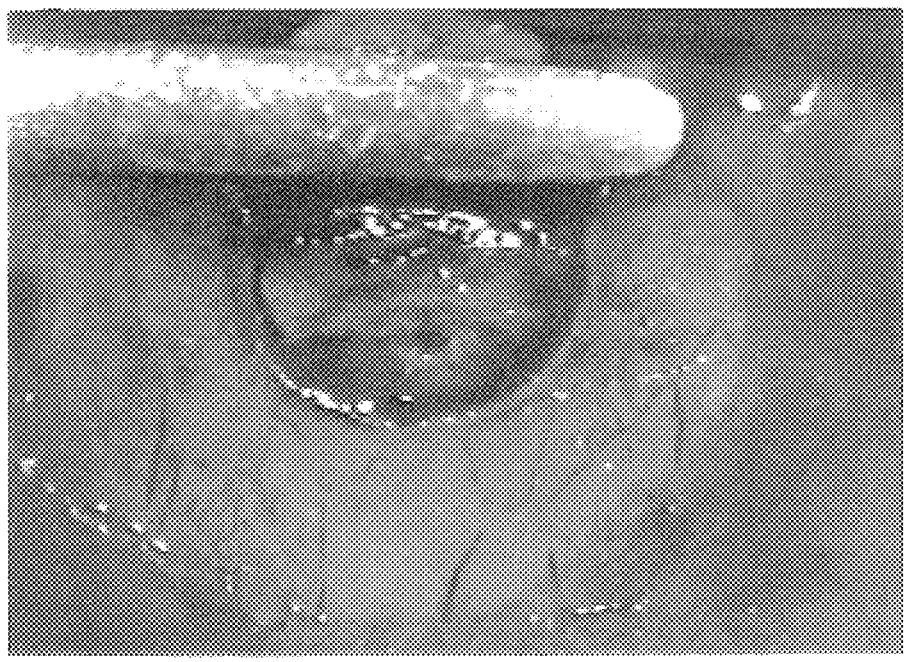
FIG. 6 shows the flap bent over the cornea and the trabeculum area exposed.

6. Once the flap is dissected (FIG. 5) it is bent over the cornea and is covered by a spatula to protect it from the excimer rays.

7. Ablation of the deep wall (scleral floor) takes place, preferably with a GSS or opening variable delivery system, to effect plane lathing in successive layers of 0.25 to 2 microns, depending on the PTK software employed to control operation of the laser. This type of action allows a progressive thinning of exposed corneal and scleral layers that enables the ablation of the Schlemm channel as well as the partial trabecular meshwork.

Figure 7:
FIG. 7 shows the excimer lathing on the trabeculum.
Figure 8:
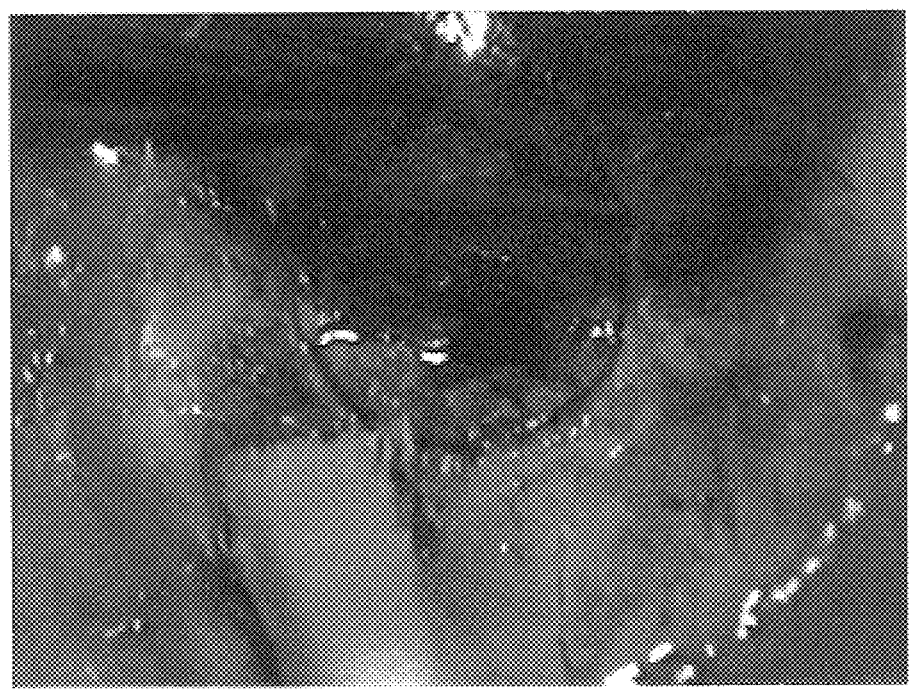
FIG. 8 shows the beginning of the aqueous humor filtration.
Figure 9:
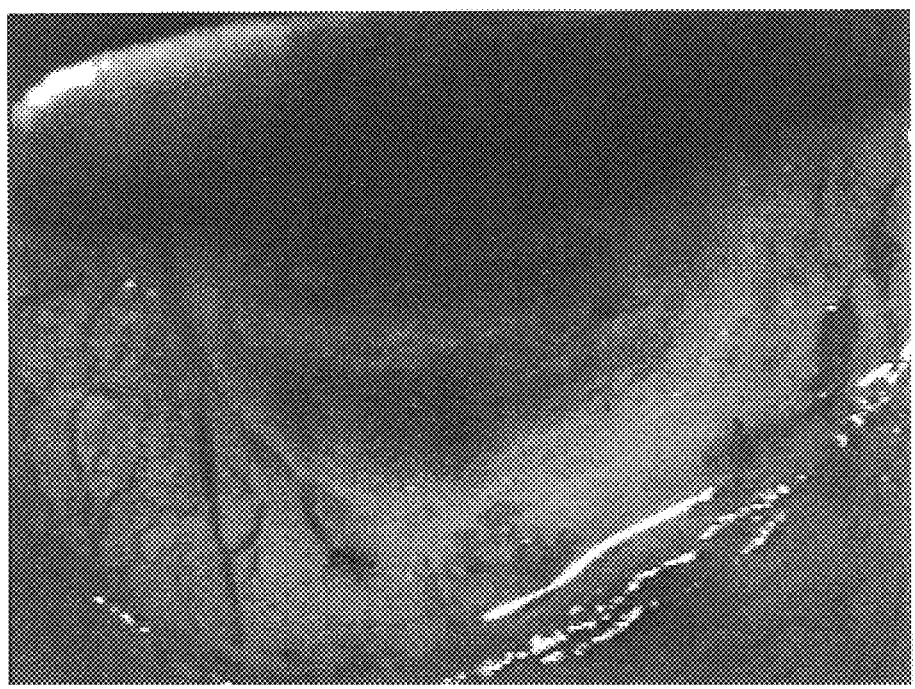
FIG. 9 is a magnified view of the aqueous humor filtration.

8. The ablation is perfectly controlled and lets the aqueous humor flow from the anterior chamber (this follows the Arenas Archilla procedure performed with a mechanical diamond drill) )FIGS. 7, 8, 9).

Figure 10:
FIG. 10 shows a hole in the Descemet membrane as revealed by an aqueous humor drop.
Figure 11:
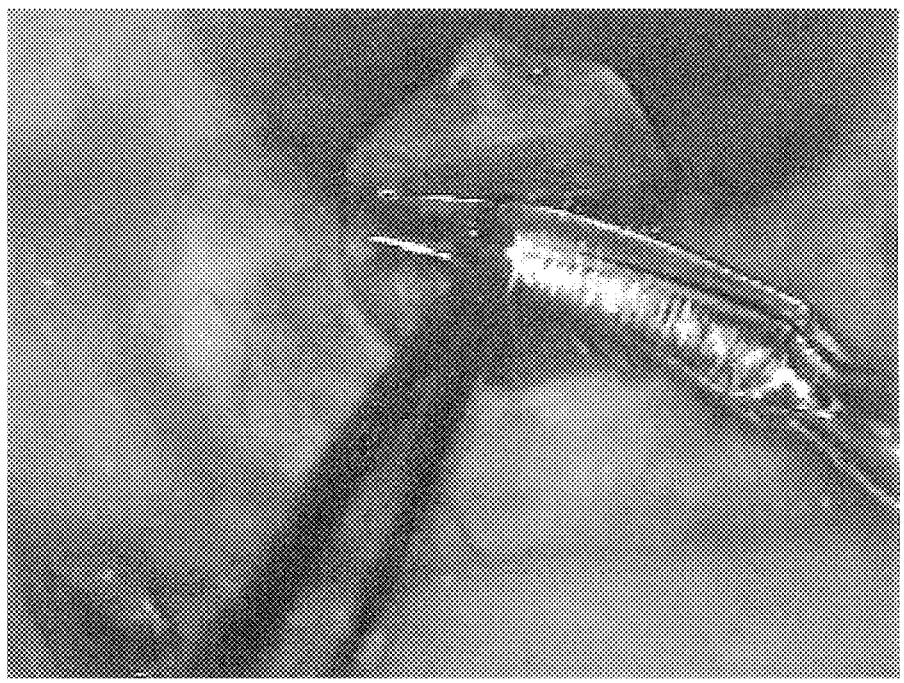
FIG. 11 illustrates basal iridectomy.

9. Iridectomy: At this time, the excimer laser energy can be applied again up to the moment of producing a microperforation of corneal tissue. This is evident when an aqueous humor drop appears in that place (FIG. 10). This enables the surgeon to practice a small basal iridectomy (FIG. 11) that if it were not done at this time, would have to be performed either previous to surgery or as a secondary procedure with a Yag laser.

This microperforation of the Descemet membrane does not create any risk of intrasurgical infection if asepsis is good. Descemet membrane tears close in a few days and thus there is little probability of a late infection.

Postoperative effects with LTD has less inflammatory reaction than with the trabeculectomy. As is known, any surgical procedure produces a certain amount of inflammation and in cases of shallow chamber there is a risk of potential anterior sinequiae.

A basal iridectomy balances pressures between anterior and posterior chambers, thus diminishing the possibility of contact between the iris and the trabeculum.

Figure 12:
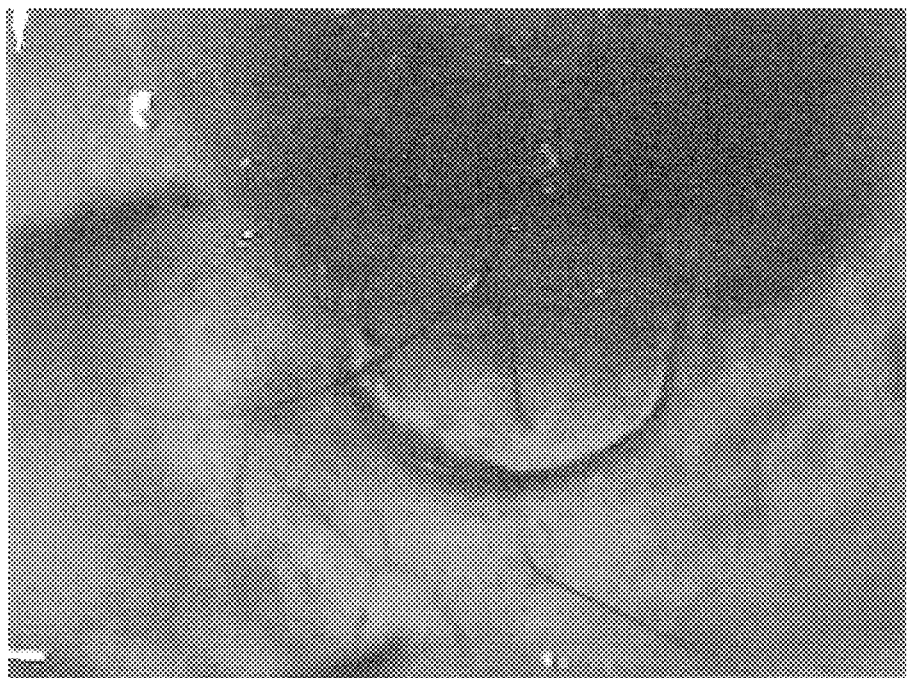
FIG. 12 shows the stitch that involves cornea-flap and posterior scleral border.
Figure 12A:
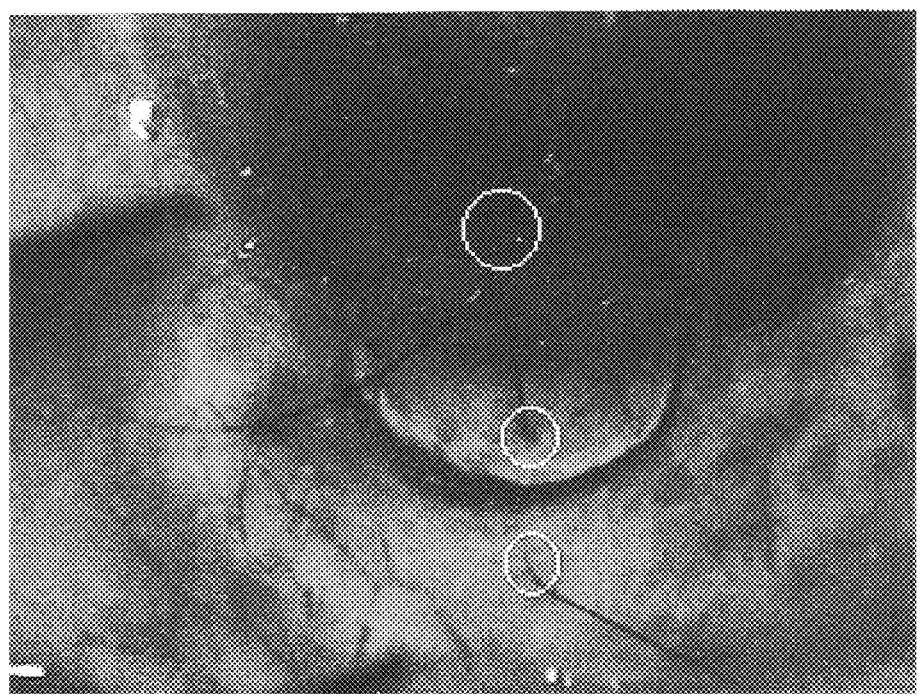
FIG. 12A is the same view as FIG. 12 with each part marked.
Figure 13:
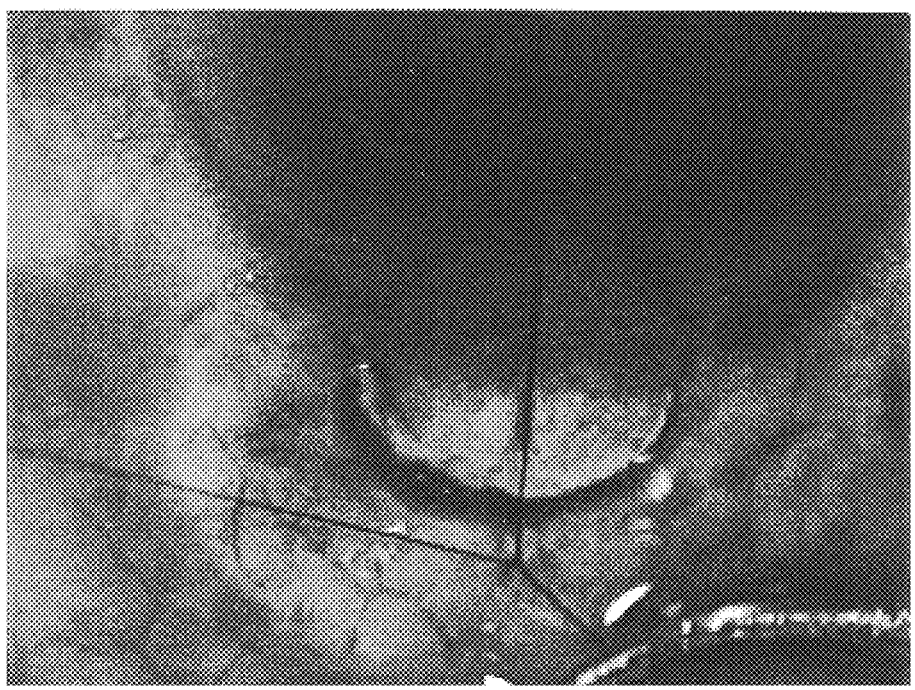
FIG. 13 shows the stitch that temporarily closes the scleral flap.
Figure 14:
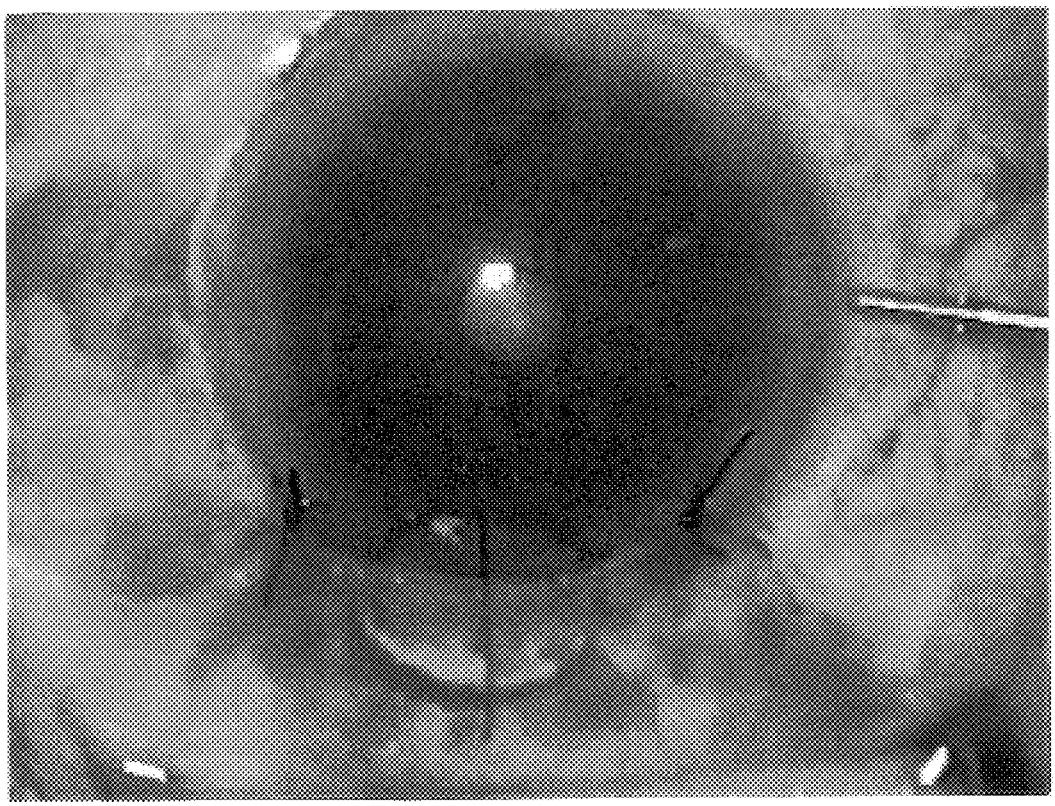
FIG. 14 shows the conjuctiva already sutured, and through the paracenthesis the filtration proves being adequate.

10. When the procedure is over, the scleral flap is repositioned to be sutured, preferably with a 10-0 nylon stitch that pierces successive corneal stroma to 1.5 mm of the limbus, through the central posterior scleral flap border and the border distal from the sclera (FIGS. 12, 13, 14). This stitch may be removed in any postoperative check-up to reopen the scleral flap borders to improve filtration, if necessary.

The semicircular 4.25×3 mm flap can be cut (only 1 mm) in its posterior portion leaving the sclerotomy open. This makes closure difficult, thus improving filtration.

11. The conjuctiva is respositioned and sutured with two stitches anchored to the limbar episclera (FIG. 14).

12. By the paracenthesis (1st step), after the scleral ablation is finished and the surgery over, salt balanced solution is injected to test the filtration is adequate and to reform the anterior chamber (FIG. 14).

Eight cases of laser trabeculodissection or ab-outer trabeculectomy were performed with the described technique of the invention using the Minicompact 200 excimer laser. The results are described in Table I.

Neither of the commonly used drugs 5-F nor Mitomicin was added during the procedure. Results of the procedure were satisfactory, with all the eyes maintaining their intraocular pressures below 20 mmHg. Thirty-seven (37%) percent of the cases needed additional medical treatment of Timolol 0.5% and Pilocarpine 1% twice a day.

Average previous intraocular pressure was 31 mmHg, twelve within a range of 19–68 mmHg.

Postoperative average intraocular pressure was 14 mmHg within a range of 8–19 mmHg.

Case in which iridectomy was not performed had to be re-operated completing LTD and iridectomy. The patient had a controlled intraocular pressure without medication. In this case, the scleral flap was triangular.

In summary, the surgical procedure of the invention can be carried out under topical anesthesia. The technique includes:

(a) Paracenthesis (b) A lumbar or fornix based conjunctival incision (c) Making a scleral flap (triangular, rectangular or semicircular)

(d) Trabeculodissection of 4×2.3 mm using the galvanometric scanning laser delivery system, or opening variable delivery system with a PTK software, ablating the Schlemm channel as well as the trabeculum up to the moment the aqueous humor flows without difficulty.

(e) Proceeding with ablation until a small hole is produced in the adjacent cornea through which a basal iridectomy is manually performed.

(f) Repositioning and suture of the scleral flap, such as with a 10-0 nylon stitch, that involves cornea, the posterior flap border and the distal sclera so that the stitch can be removed later if it is needed.

(g) The semicircular 4.25×3 mm flap can be cut (only 1 mm) in its posterior portion leaving the sclerotomy open to make closure difficult to improve filtration.

(h) Conjunctival suture.

Using the surgical technique of the invention provides a number of important advantages:

1. It allows LTD to be performed with topical anesthesia, lessening intrasurgical risks and shortening recovery time.

2. It allows a partial, or completely extraocular, surgery to be performed without opening the anterior chamber, thus preventing decompressing effects that may result in a vitreous loss, or even an expulsive hemorrhage.

3. It performs the ablation of the Schlemm channel and a great part of the trabeculum in a 4×2 mm area similar to the ablation described for trabeculectomy.

4. Iridectomy performed through the minimum hole in the Descemet membrane adjacent to the trabeculum, helps to balance the anterior and posterior chamber pressures, and mainly in the LTD areas, thus preventing anterior sinequiae.

5. The posterior border of the scleral flap may be cut 1 mm to make healing difficult and maintain the sclerotomy open, with the consequent improvement in filtration level.

6. Paracenthesis does not add any intrasurgical risk of infection and allows a check up on filtration and reforming of the anterior chamber with balanced salt solution.

7. The corner-flap-scleral stitch allows a transitory closure of the lamellar sclerectomy to prevent a low chamber due to excess filtration.

The ablation can be carried out by Planar Phototherapeutic Keratechtomy.

Specific features of the invention are shown in one or more of the drawings for convenience only, as each feature may be combined with other features in accordance with the invention. Alternative embodiments will be recognized by those skilled in the art and are intended to be included within the scope of the claims.

All cited documents are incorporated by reference in their entirety. In case of conflict, the present specification controls.

I claim:

1. A method of performing laser surgery in the eye of a patient to treat glaucoma comprising the steps of:
   a. making an opening to expose the treatment area of trabecular meshwork;
   b. performing trabeculodissection
   c. making a peripheral iridectomy.

2. The method as in the claim 1 wherein the opening of step a. is made by forming a scleral flap.

3. The method as in claim 2 further comprising the step of closure of the sclerotomy with a removable suture.

4. The method as in claim 1 wherein treatment with the laser uses an excimer laser.

5. The method as in claim 1 wherein the opening of the treatment area is in space that includes a portion of about 4 mm×2.3 mm of the Schlemm channel and to the trabecular meshwork.

6. The method as in claim 2 wherein the opening of the treatment area exposed portion of the Schlemm channel and trabeculum is about 4 mm×2.3 mm.

7. The method as in claim 2 wherein the treating of the area of step b. is in the area of the bed of the scleral flap in a zone of about 4 mm×2.3 mm.

8. The method as in claim 1 wherein the ablation of step b. is carried out to remove tissue in successive layers.

9. The method as in claim 8 wherein said removed layers of tissue are in the range of 0.25 microns to 2 microns thick.

10. The method as in claim 8 wherein treatment with the laser uses an excimer laser.

11. The method as in claim 10 wherein said removed layers of tissue are in the range of from about 0.25 microns to 2 microns thick.

12. The method as in claim 1 further comprising the step of producing a small hole in the adjacent cornea and performing a basal iridectomy.

13. The method as in claim 2 further comprising the step of closing the scleral flap with a removable corner-flap-scleral stitch.

14. The method as in claim 1 wherein the laser utilizes a galvanometric scanning system or an opening variable delivery system.

15. The method as in claim 14 wherein treatment with the laser uses an excimer laser.

16. The method as in claim 15 wherein said the ablating is carried out to remove layers of tissue in the range of from about 0.25 microns to 2 microns thick.

17. The method as in claim 1 further comprising the step of applying a topical anesthesia prior to step a.

18. The method as in claim 6 wherein the the ablating is carried out in step b. to remove tissue in successive layers.

19. The method as in claim 1 wherein the ablation of step b. is carried out by planar phototherapeutic keratechtomy.

* * * * *